(12) United States Patent
Kondo et al.

(10) Patent No.: US 8,225,684 B2
(45) Date of Patent: Jul. 24, 2012

(54) METHODS FOR DETECTING PARTICULATES IN A HONEYCOMB FILTER

(75) Inventors: Jungo Kondo, Miyoshi (JP); Yuichi Iwata, Nagoya (JP); Tetsuya Ejiri, Kasugai (JP)

(73) Assignee: NGK Insulators, Ltd., Aichi-Prefecture (JP)

(*) Notice: Subject to any disclaimer, the term of this patent is extended or adjusted under 35 U.S.C. 154(b) by 0 days.

(21) Appl. No.: 13/187,068

(22) Filed: Jul. 20, 2011

(65) Prior Publication Data

US 2011/0271740 A1    Nov. 10, 2011

Related U.S. Application Data

(63) Continuation of application No. PCT/JP2011/057068, filed on Mar. 16, 2011.

(30) Foreign Application Priority Data

Mar. 24, 2010   (JP) .................................. 2010-067225

(51) Int. Cl.
    *B01D 35/143*   (2006.01)
(52) U.S. Cl. ............................ 73/865.8; 210/85; 210/87
(58) Field of Classification Search ................. 73/865.8; 210/85, 90
    See application file for complete search history.

(56) References Cited

U.S. PATENT DOCUMENTS

| | | | | |
|---|---|---|---|---|
| 4,477,771 A | * | 10/1984 | Nagy et al. ..................... 324/636 |
| 4,869,944 A | * | 9/1989 | Harada et al. .................. 428/116 |
| 5,062,911 A | * | 11/1991 | Hampton et al. ........... 156/89.14 |
| 5,157,340 A | * | 10/1992 | Walton et al. ................. 324/641 |
| 5,497,099 A | * | 3/1996 | Walton .......................... 324/641 |
| 6,104,032 A | * | 8/2000 | Means et al. ............... 250/341.7 |

(Continued)

FOREIGN PATENT DOCUMENTS

GB          2416836 A   *   2/2006

(Continued)

OTHER PUBLICATIONS

Miyamaru, F., Hangyo, M., "Polarization response of two-dimensional metallic photonic crystals studied by terahertz time-domain spectroscopy," Applied Optics, 2004, vol. 43, No. 6, pp. 1412-1415.

(Continued)

*Primary Examiner* — David Rogers
(74) *Attorney, Agent, or Firm* — Cermak Nakajima LLP; Tomoko Nakajima (57) ABSTRACT

A ceramic honeycomb filter including trapping holes forming lattices is used to detect particulates trapped in the filter. An electromagnetic wave is transmitted to the filter in a plane perpendicular to the longitudinal direction of the trapping hole. The electromagnetic wave after the electromagnetic wave passes through the filter is received and the particulates trapped in the filter are detected on the base of a received intensity of the electromagnetic wave. The electromagnetic wave has a frequency of 0.294 c/a or more and c/a or less (a represents a lattice spacing of said trapping holes and c represents the speed of light). The electromagnetic wave is irradiated to the filter wherein the particulates are not trapped and an inclined angle θ of the electromagnetic wave with respect to the lattices is changed so as to increase a received intensity of the electromagnetic wave.

22 Claims, 11 Drawing Sheets

U.S. PATENT DOCUMENTS

| | | | |
|---|---|---|---|
| 7,157,919 B1 * | 1/2007 | Walton | 324/641 |
| 7,253,641 B2 * | 8/2007 | Knitt et al. | 324/639 |
| 7,276,101 B2 * | 10/2007 | Ichikawa | 55/523 |
| 7,410,528 B2 * | 8/2008 | Rae et al. | 95/273 |
| 7,614,304 B2 * | 11/2009 | Gunasekaran et al. | 73/598 |
| 7,648,549 B2 * | 1/2010 | Gargano et al. | 55/523 |
| 7,674,309 B2 * | 3/2010 | Gargano et al. | 55/523 |
| 7,679,374 B2 * | 3/2010 | Bromberg et al. | 324/637 |
| 7,849,747 B2 * | 12/2010 | Owens | 73/598 |
| 7,870,779 B2 * | 1/2011 | Lattin et al. | 73/114.69 |
| 2005/0247131 A1 * | 11/2005 | Breuer | 73/579 |
| 2006/0188398 A1 | 8/2006 | Yano et al. | |
| 2007/0199380 A1 * | 8/2007 | Daoud | 73/596 |
| 2007/0266790 A1 * | 11/2007 | Gunasekaran et al. | 73/624 |
| 2009/0120189 A1 * | 5/2009 | Fei et al. | 73/596 |
| 2010/0025586 A1 | 2/2010 | Ogawa et al. | |
| 2010/0187089 A1 | 7/2010 | Daido et al. | |
| 2010/0201562 A1 | 8/2010 | Kondo et al. | |

FOREIGN PATENT DOCUMENTS

| | | |
|---|---|---|
| JP | 2005-099007 A | 4/2005 |
| JP | 2007-079466 A | 3/2007 |
| JP | 2009-002276 A | 1/2009 |
| JP | 2009-057948 A | 3/2009 |
| JP | 2009-250062 A | 10/2009 |
| WO | WO2008/093729 A1 | 8/2008 |
| WO | WO2009/031600 A1 | 3/2009 |

OTHER PUBLICATIONS

Liu, C. S., Peng, L.-M., "Optical response of one-dimensional ordered mesoporous materials," Physical Review B, Condensed Matter and Materials Physics, 2002, vol. 66, No. 19, pp. 193407.1-193407.3.

International Search Report and Written Opinion for PCT Patent App. No. PCT/JP2011/057068 (Jun. 7, 2011).

* cited by examiner

METHODS FOR DETECTING PARTICULATES IN A HONEYCOMB FILTER

This application is a continuation of, and claims priority under 35 U.S.C. §120 to, International Patent Application No. PCT/JP2011/057068, filed on Mar. 16, 2011, which claims priority under 35 U.S.C. §119 to Japanese Patent Application No. 2010-067225, filed Mar. 24, 2010, both of which are incorporated by reference.

TECHNICAL FIELD

The present invention relates to a method for detecting particulates, which may be used for detection of PM accumulation amount in a filter disposed in an exhaust system of an internal combustion engine such as a diesel engine or the like.

BACKGROUND ARTS

Toxic substances in the internal combustion engine, such as a diesel engine, are discharged as PM (particulate matter: soot composed of carbon fine particles, high-molecular weight hydrocarbon fine particles, sulfur-based fine particles such as sulfate, etc.). Since the Environmental Agency recently has considered deciding an environmental criterion with respect to fine particulates with particle size of 2.5 μm or less to more strictly regulate particulates, a development race, for example, of systems for controlling exhaust gas for a diesel engine or for PM monitoring, has been performed to respond to the stricter regulations.

As an exhaust emission control system for diesel engine, a sealed type ceramic honeycomb body (diesel PM filter: DPF) is prevalent. The DPF has a ceramic honeycomb structure in which both ends of opening parts of cells are alternately sealed. That is, the DPF includes inflow-side cells sealed on exhaust gas downstream side, outflow-side cells sealed on exhaust gas upstream side, and a cell partition wall defining the inflow-side cells and the outflow-side cells, respectively. The particulates are trapped by passing exhaust gas through pores of the cell partition wall.

However, since accumulation of the particulates causes increase in pressure loss of exhaust gas in the DPF, the DPF must be regenerated by removing the accumulated particulates to suppress deterioration of output or fuel consumption in the internal combustion engine. Therefore, forced regeneration of the DPF is being performed by burning the accumulated PM, for example, according to the following process. That is, the temperature of exhaust gas is raised by adding a reducing agent, such as fuel, to the exhaust gas, the reducing agent is burned with an oxidation catalyst disposed on the upstream side of the DPF, and the resulting high-temperature exhaust gas is then supplied to the DPF.

However, when such a regeneration control is performed in a state where the particulates are trapped within the filter in an accumulation amount beyond a certain filter use limit value, cracking or melting loss of the filter is caused by localization of temperature or excessive rise of overall temperature of the filter resulting from the burning of PM. For preventing such a failure, prediction of accumulation amount of particulates within the filter is performed by measuring the pressure loss in the filter, an intake air quantity, an exhaust gas temperature, a fuel injection quantity, an EGR opening, an engine rate or the like and performing arithmetic processing thereto in ECU.

On the other hand, in a common internal combustion engine such as the diesel engine, a value is obtained by multiplying a safety ratio to this filter use limit value and then adopted as a regeneration control point. The point is generally represented by:

Regeneration control point (g/L)=filter use limit value (g/L)×safe factor, wherein the safe factor is 0<safe factor<1. Accordingly, the regeneration control point is set so as to satisfy the relationship of:

Regeneration control point (g/L)<filter use limit value (g/L).

This safety factor is differently set by each automobile maker, and is determined according to the completion rate of prediction technique for accumulation amount of particulates in the filter or the guideline for safety of each maker. As the safety factor is closer to 1, the filter regeneration becomes less frequent, so that the fuel efficiency is less deteriorated. Therefore, the accumulation amount of particulates in the filter needs to be accurately predicted.

In Japanese Patent Publication No. 2009-2276A, a transmitting antenna and a receiving antenna are mounted on a center part of an outer wall of a DPF filter so as to be opposed to each other. An electromagnetic wave of several tens GHz to several tens THz is transmitted from the transmitting antenna, passed through the filter, and received by the receiving antenna mounted on the opposite side. The accumulation amount of particulates to the filter is thereby calculated based on the receiving intensity of the electromagnetic wave. The electromagnetic wave is irradiated through an outer side wall of the filter in the direction perpendicular to the trapping holes of the filter.

Further according to Japanese Patent Publication No. 2009-250062A, electromagnetic wave is irradiated from an outer side wall of the filter in the direction perpendicular to the trapping holes of the filter.

According to Japanese Patent Publication No. 2009-57948A, electromagnetic wave is irradiated through an outer side wall of the filter in the direction perpendicular to the trapping holes of the filter. Further, the electromagnetic wave is irradiated to a plurality of positions on the side wall of the filter to detect the outgoing electromagnetic waves from a plurality of positions of the filter responsive to those, so that distribution of accumulation amounts in the filter is measured.

According to WO 2008/093729A1, it is described that electromagnetic wave is irradiated to a mesh made of a conductor while the optical axis of the electromagnetic wave is slightly inclined with respect to the mash plane to improve the received intensity of the electromagnetic wave.

Besides, Japanese Patent Publication No. 2007-79466A discloses a device of generating electromagnetic wave having thin plate structure.

SUMMARY OF THE INVENTION

According to methods described in Japanese Patent Publication Nos. 2009-2276A, 2009-250062A and 2009-57948A, the transmitting and receiving means are provided on a side wall of a container of a DPF filter, that is ceramic honeycomb filter to oppose each other, and electromagnetic wave having a frequency of several tens GHz to several tens THz is irradiated to the side wall of the filter so as to pass across the filter. The electromagnetic wave is thus damped after passing through particulates present in the cross section of the filter. According to the Examples, electromagnetic wave having a frequency of 600 GHz is irradiated so as to pass across the filter to assume an accumulation amount of soot.

However, the inventors have carried out experiments based on these methods and found a novel phenomenon which has not been known yet. That is, it was tried to increase the wavelength of the electromagnetic wave to improve the efficiency of measurement. It was, however, proved that the intensity of the electromagnetic wave after the transmission through the honeycomb filter is considerably changed depending on an angle of incidence, as the wavelength $\lambda$ of the electromagnetic wave approaches the lattice spacing a of the ceramic honeycomb filter. Even in the case of a blank that particulates are not trapped in trapping holes of the ceramic honeycomb filter, it was considerably changed the intensity of the electromagnetic wave transmitting through the honeycomb filter. Such findings have not been known in a method of detecting particulates using a ceramic honeycomb filter.

An object of the present invention is, based on the findings, to improve a transmittance of electromagnetic wave in a ceramic honeycomb filter which does not trap particulates so as to improve a detection sensitivity when the particulates are trapped.

The invention provides a method using a ceramic honeycomb filter comprising trapping hole, forming lattices, for trapping the particulates from a gas containing the particulates to detect the particulates trapped in the ceramic honeycomb filter. The method comprises:

transmitting an electromagnetic wave to the filter in a plane perpendicular to the longitudinal direction of the trapping hole, receiving the electromagnetic wave after the electromagnetic wave passes through the filter, detecting the particulates trapped in the filter based on a received intensity of the electromagnetic wave, wherein the electromagnetic wave has a frequency of greater than or equal to 0.294 c/a or less than or equal to 1 c/a (a represents a lattice spacing of the trapping holes and c represents the speed of light), and irradiating the electromagnetic wave to the filter wherein the particulates are not trapped and changing an inclined angle of the electromagnetic wave with respect to the lattices so as to increase a received intensity of the electromagnetic wave.

The present invention further provides a method using a ceramic honeycomb filter comprising trapping holes for trapping the particulates from a gas containing the particulates to detect the particulates trapped in the filter, wherein each of the trapping holes forms a square lattice divided by opposing first and second walls and opposing third and fourth walls. The method comprises:

transmitting an electromagnetic wave to the filter in a plane perpendicular to the longitudinal direction of the trapping hole, receiving the electromagnetic wave after the electromagnetic wave passes through the filter, and detecting the particulates trapped in said filter based on a received intensity of the electromagnetic wave, wherein the following relationships are satisfied:

$a/\lambda \geq 0.294$;

$a/\lambda \leq 0.294 + 4.9 \times 10^{-3} \times \theta$; and $a/\lambda \leq 0.735 - 4.9 \times 10^{-3} \times \theta$ (a represents a lattice spacing of the trapping holes, $\lambda$ represents a wavelength of the electromagnetic wave, and $\theta$ represents an inclined angle of said electromagnetic wave with respect to an axis perpendicular to the first and second walls).

More preferably, $\theta$ is 30° or more, and 60° or less.

Further, the present invention provides the above method wherein the following relationships are satisfied:

$0.441 + 4.9 \times 10^{-3} \times \theta \leq a/\lambda \leq 0.735 - 4.9 \times 10^{-3} \times \theta$; and $0 \leq \theta$ More preferably, $\theta$ is 30° or less.

Further, the present invention provides the above method wherein the following relationships are satisfied:

$0.882 - 4.9 \times 10^{-3} \times \theta \geq a/\lambda \leq 0.294 - 4.9 \times 10^{-3} \times \theta$; and $\theta \leq 90°$ More preferably, $\theta$ is 60° or more.

Further, the present invention provides the above method wherein the following relationships are satisfied:

$0.782 - 4.9 \times 10^{-3} \times \theta \leq a/\lambda \leq 0.882 - 4.9 \times 10^{-3} \times \theta$; and $10° \leq \theta \leq 30°$ Further, the present invention provides the above method wherein the following relationships are satisfied:

$0.343 + 4.9 \times 10^{-3} \times \theta \leq a/\lambda \leq 0.441 + 4.9 \times 10^{-3} \times \theta$; and $60° \leq \theta \leq 80°$ Further, the present invention provides the above method wherein the following relationships are satisfied:

$0.784 \leq a/\lambda \leq 0.98$; and $35° \leq \theta \leq 55°$

According to the present invention, electromagnetic wave is irradiated to a ceramic honeycomb filter, which does not trap particulates, from the side of a side wall of the filter while the inclined angle of the electromagnetic wave with respect to lattices is changed, so that it is possible to select measuring points or ranges where the transmittance of the electromagnetic wave becomes high. It is thus possible to improve the detection sensitivity, by fixing the positional relationship of the filter and electromagnetic wave and then measuring an amount of trapped particulates.

Further, the inventors tried to irradiate electromagnetic wave to a ceramic honeycomb filter at various angle of incidences $\theta$ so that the a received intensity was measured. As a result, in a range of high frequency of the electromagnetic wave, it is proved that an angle required for the transmittance is changed and the optimum range of the angle is observed in the frequency range. In this case, the optimum range of the angle of incidence is not changed while the lattice spacing a is made constant and the wall thickness r is changed.

Figure 6:
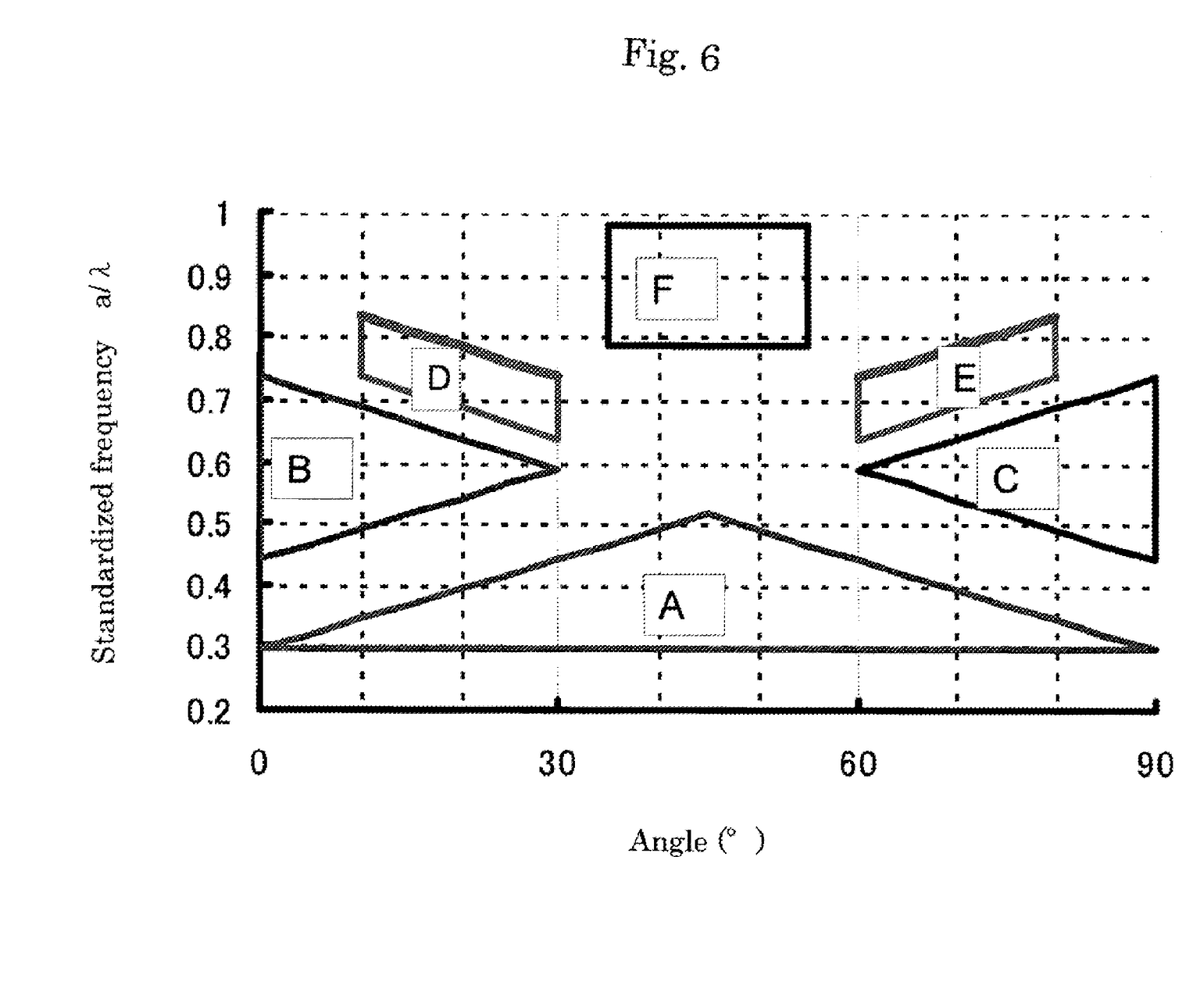
FIG. 6 is a graph showing relationship of an angle of incidence of electromagnetic wave and standardized frequency.

Actually, as shown in FIG. 6, it is considerably reduced a loss of the electromagnetic wave transmitting the ceramic honeycomb filter with in regions A, B, C, D, E and F defined in claims 3 to 8, respectively.

It is further proved that this characteristics does not depend on the wall thickness r of the filter and can be standardized referring to the lattice spacing a and frequency f.

BRIEF DESCRIPTION OF THE DRAWINGS

FIG. 4 (a) is a perspective view schematically showing a filter 11, and FIG. 4 (b) is a plan view schematically showing the filter 11.

EMBODIMENTS OF THE INVENTION

The present invention will be described further in detail referring to drawings below.

Figure 1:
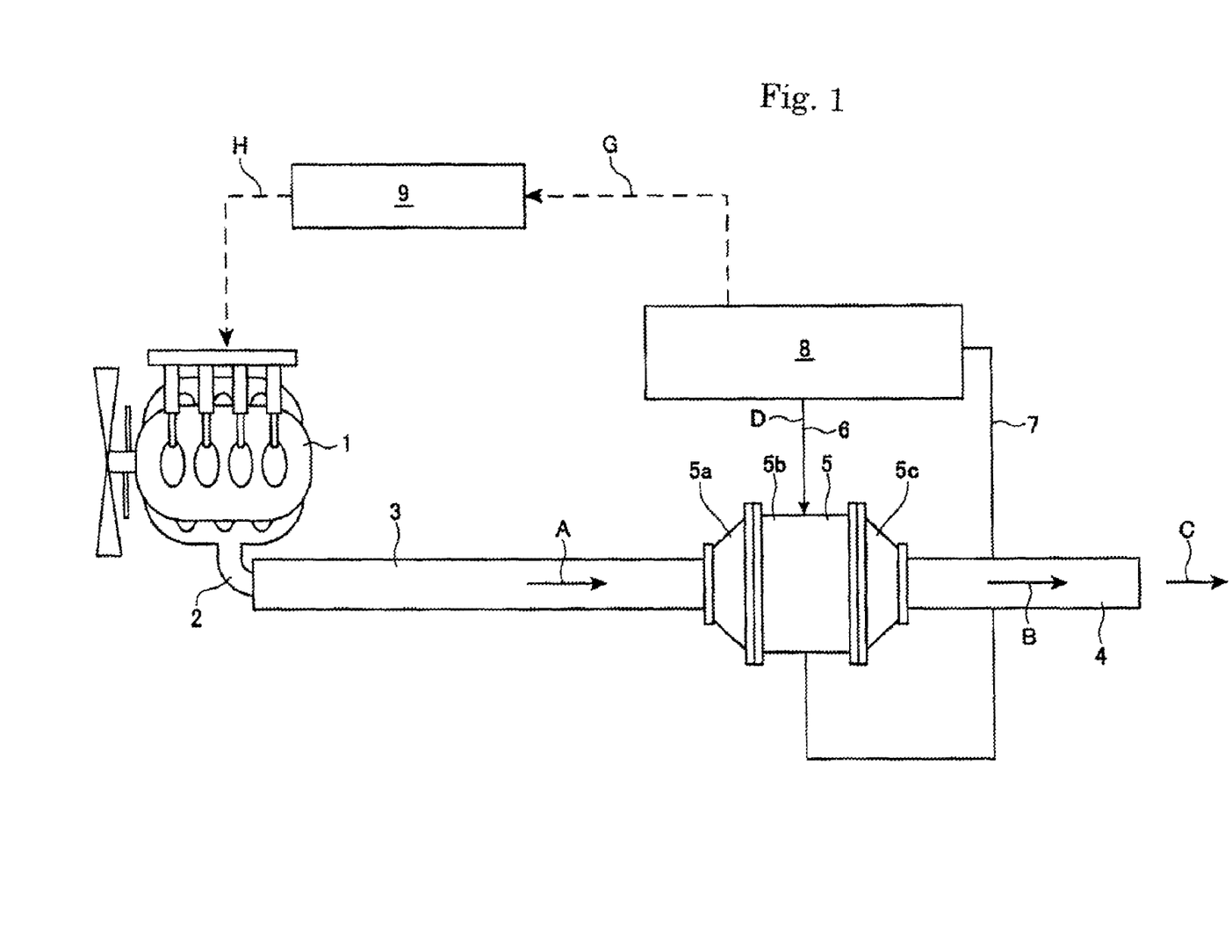
FIG. 1 is a block diagram schematically showing a device for detecting an accumulation amount of particulates according to the present invention.
Figure 2:
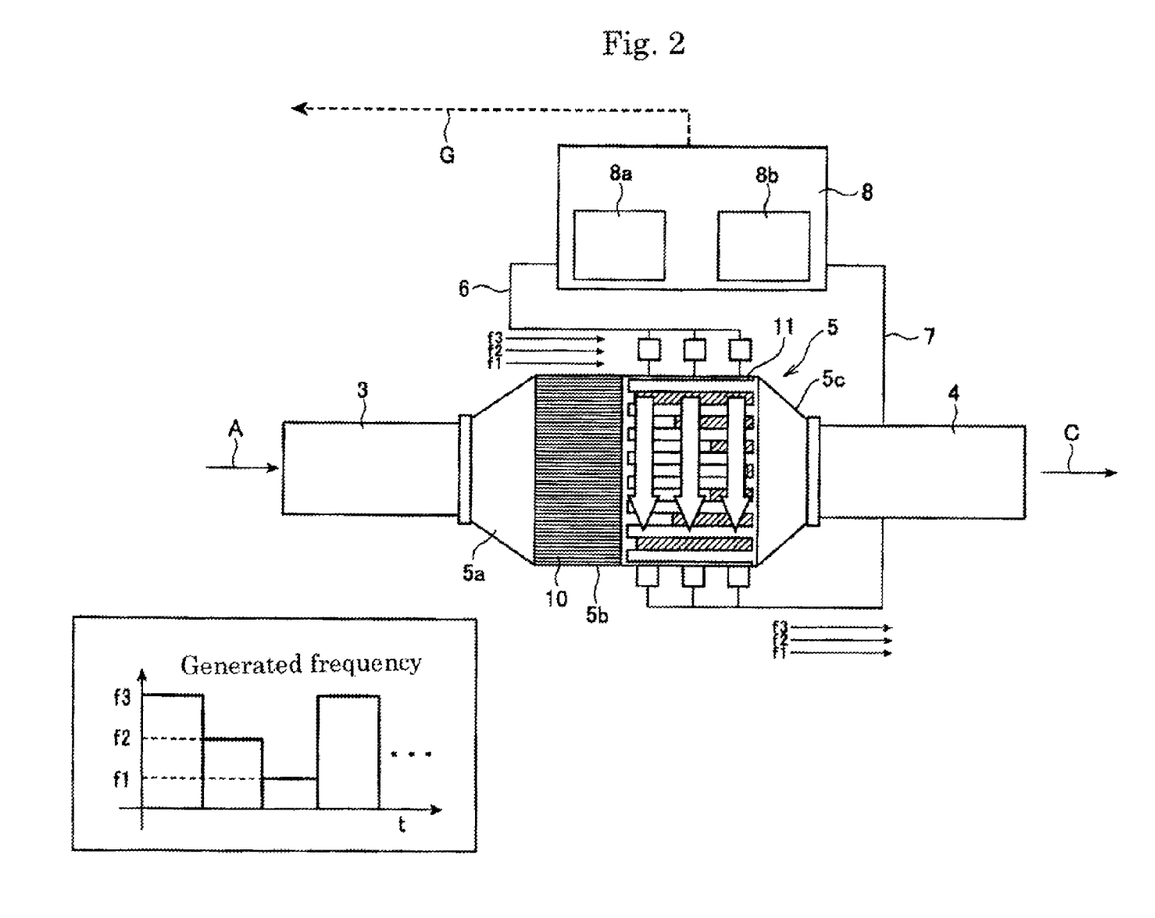
FIG. 2 is a partially enlarged cross-sectional view showing an area around a filter and a container applicable in the present invention.

FIG. 1 schematically shows an exhaust emission control system. An exhaust pipe 2 of an exhaust manifold of a diesel engine 1 is connected to a container 5 through an upstream pipe 3. A downstream pipe 4 is provided on the downstream side of the container 5. The container 5 includes, as shown in FIG. 2, a storage part 5b with a constant inside diameter for storing a ceramic honeycomb filter, an upstream connection part 5a and a downstream connection part 5c.

An oxidizing catalyst 10 and a filter 11 are stored within the storage part 5b of the container 5. The filter 11 is composed of a porous ceramic honeycomb structure having a number of pores regularly formed therein. A part of the pores is sealed on the exhaust gas downstream side to form inflow-side cells, and the remainder thereof is sealed on the exhaust gas upstream side to form outflow-side cells. The inflow-side cells and the outflow-side cells are formed to be alternately adjacent to each other, whereby a honeycomb-shaped wall flow structure is constituted.

A plurality of transmitting means is provided on the side of a side face of a container 1 and connected to a transmission control unit 8a of a control unit 8 through a line 6. The transmitting means are arranged from the upstream to downstream. Further, a plurality of receiving means are provided on the side of the side face of the container 1 and connected to a reception control unit 8b of the control unit 8 through a line 7. The receiving means are arranged from the upstream to downstream. Each of the transmitting means is provided at a position opposing the respective receiving means through the filter.

Exhaust gas from the engine 1 flows in the upstream pipe 3 as shown by arrow A to enter the container 5, in which it passes the oxidizing catalyst 10 first, then passes the filter 11, then flows in the flow passage 4a of the downstream pipe 4, and discharges out as shown by arrow B. Particulates are trapped and accumulated in the filter 11.

Here, deviation tends to be observed in the accumulation amount of the particulates in the holes. For example, the amount of trapping or accumulation may be larger in the edge part and smaller in the central part of the filter.

Then, responsive to signal D from the transmission control unit 8a of the control unit 8, each of the transmitting means transmits electromagnetic wave. Here, the electromagnetic waves transmitted from the adjacent transmitting means are collimated, respectively, for avoiding the interference of them. According to a preferred embodiment, the frequencies f1, f2 and f3 of the respective electromagnetic waves are made different from each other. Further, as shown in FIG. 2, it is preferred that the respective electromagnetic waves are transmitted by time sharing system.

In this case, each transmitting means includes a band pass filter transmitting only electromagnetic wave with a specific frequency, and each transmitting means can only transmit the electromagnetic wave having the respective frequency f1, f2 or f3. Each electromagnetic wave transmitted from the corresponding transmitting means passes across the filter 11, is subjected to absorption and damping due to the filter material and particulates and then received with the corresponding receiving means.

Each of received signals f1, f2 and f3 from the corresponding receiving means is sent to the reception control unit 8b of the control unit 8 through the line 7 and then processed. Then, as shown in arrow G, information of the respective transmitted electromagnetic wave and that of the respective received electromagnetic wave are sent to a calculating unit 9. In the calculating unit 9, the information of the transmitted electromagnetic wave, such as intensity, is compared with the information, such as intensity, of the received electromagnetic wave, and it is referred information of a standard curve showing relationship of the intensity of the electromagnetic wave and accumulation amount so that the accumulation amount is calculated.

The obtained results of the calculation of the accumulation amount are outputted as arrow H for the subsequent use. For example, at the time point of the accumulation amount exceeding a threshold value, the filter 11 may be burned for the regeneration or a signal for the exchange may be outputted.

Here, due to the distribution of the particulates, the amount of damping due to the particulates is relatively small in the electromagnetic wave f1 and relatively large in the electromagnetic wave f3. Therefore, the received information by the respective electromagnetic waves f1, f2 and f3 is used for the calculation to know accumulation amounts in the corresponding regions of the filter 11. According to the example, the respective accumulation amounts can be known corresponding to the upstream, middle-stream and downstream regions of the filter 11.

According to a preferred embodiment, it is provided a main waveguide and a plurality of transmitting side waveguides connected to the main waveguide. Transmitting means are provided in the transmitting side waveguides, respectively, and a plurality of kinds of electromagnetic waves with frequencies different form each other are propagated on time sharing system to the main waveguide. At each of the transmitting side waveguides, one of the electromagnetic waves is selected, propagated and transmitted from the corresponding transmitting means. According to this embodiment, the waveguides are used to measure the special distribution of the accumulation amount in the filter without the need of complicated systems.

For selecting the frequency of the electromagnetic wave in each of the transmitting side waveguides, for example, the radius of the waveguide is adjusted to select its cut-off frequency, to cut electromagnetic waves with frequencies out of the cut-off frequency, and to propagate electromagnetic waves with the other frequencies.

Figure 3:
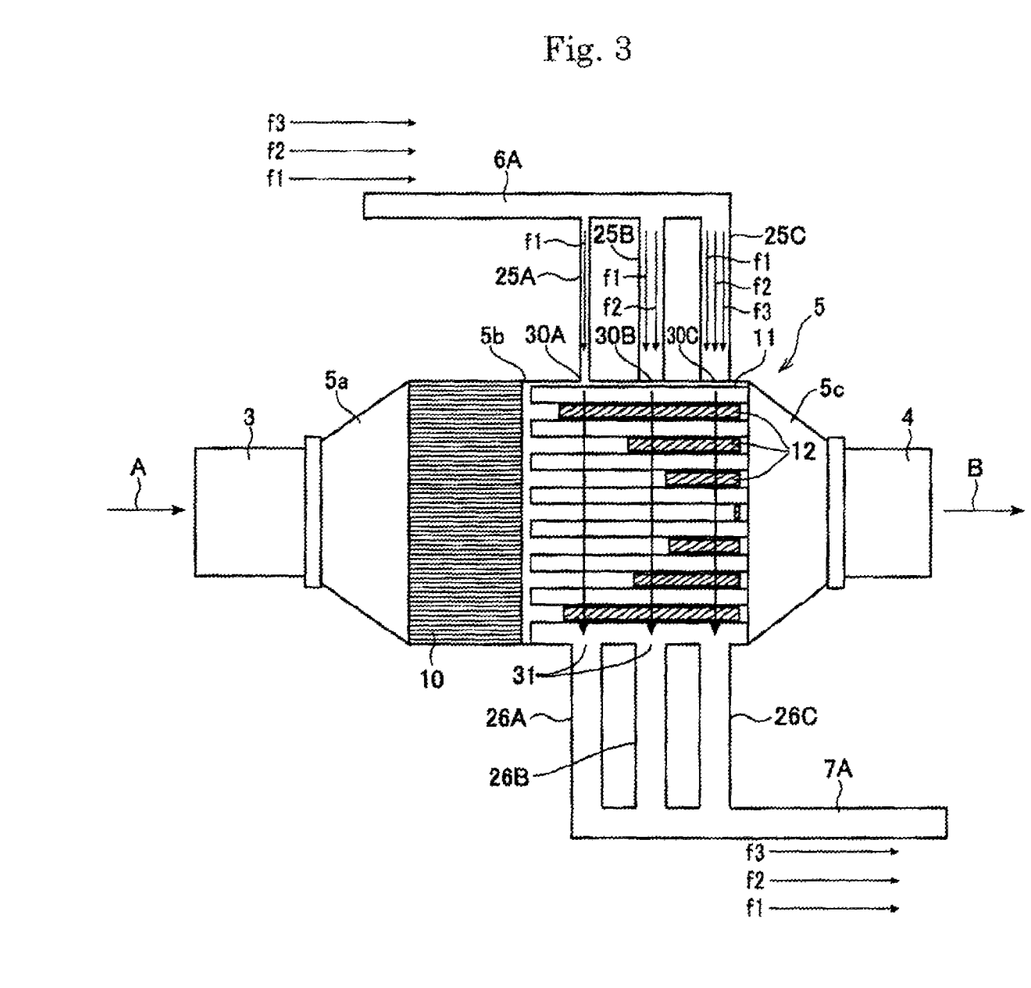
FIG. 3 is a cross sectional enlarged view showing an area around a filter and a container applicable in the present invention.

In FIG. 3, it can be measured special distribution of accumulation amount of the particulates 12. A plurality of waveguides 25A, 25B and 25C are provided on the side of a side face of a container 5 and are connected to a main waveguide 6A. The waveguides 25A, 25B and 25C are arranged from the upstream to the downstream of the filter. Further, a plurality of waveguides 26A, 26B and 26C are provided on the side of the side face of the container 5 and are connected to a main waveguide 7A. The waveguides 26A, 26B and 26C are arranged from the upstream to the downstream of the filter. The waveguides 25A, 25B and 25C are provided at positions opposing the corresponding waveguides 26A, 26B and 26C on the reception side through the filter.

Exhaust gas from the engine 1 flows in the upstream pipe 3 as shown by arrow A to enter the container 5, in which it passes the oxidizing catalyst 10 first, then passes through the filter 11 and then flows in the flow passage of the downstream pipe 4, and discharges out as shown by arrow B. Particulates are trapped and accumulated in the filter 11.

Figure 4:
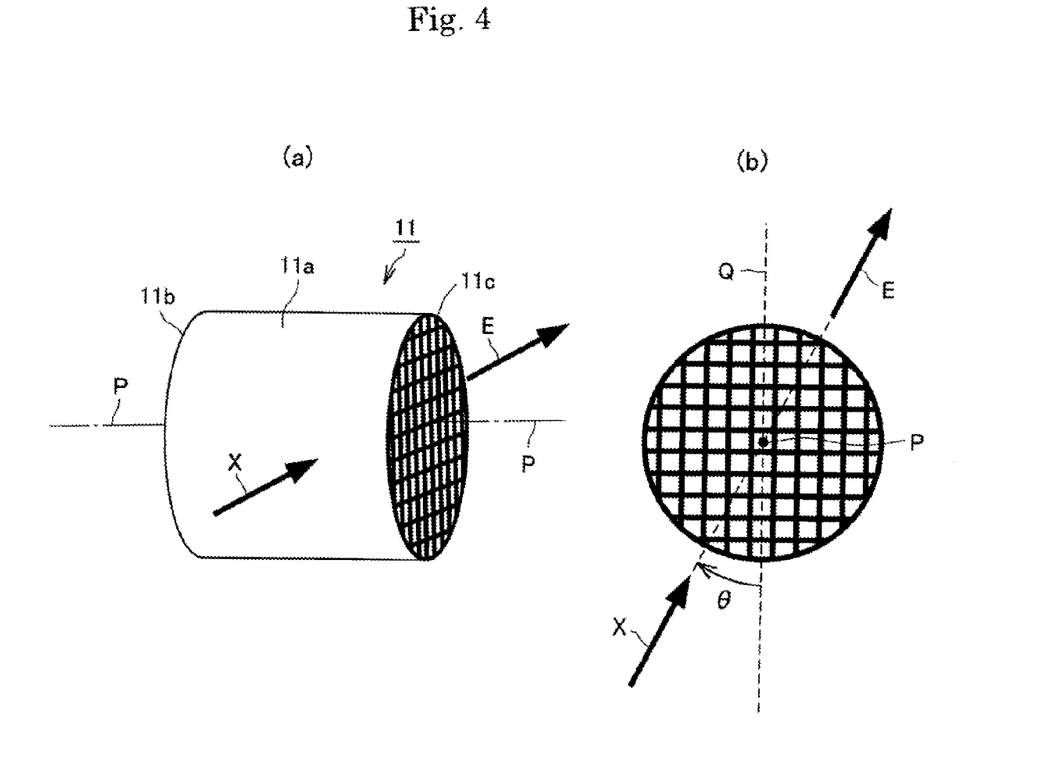
Figure 5:
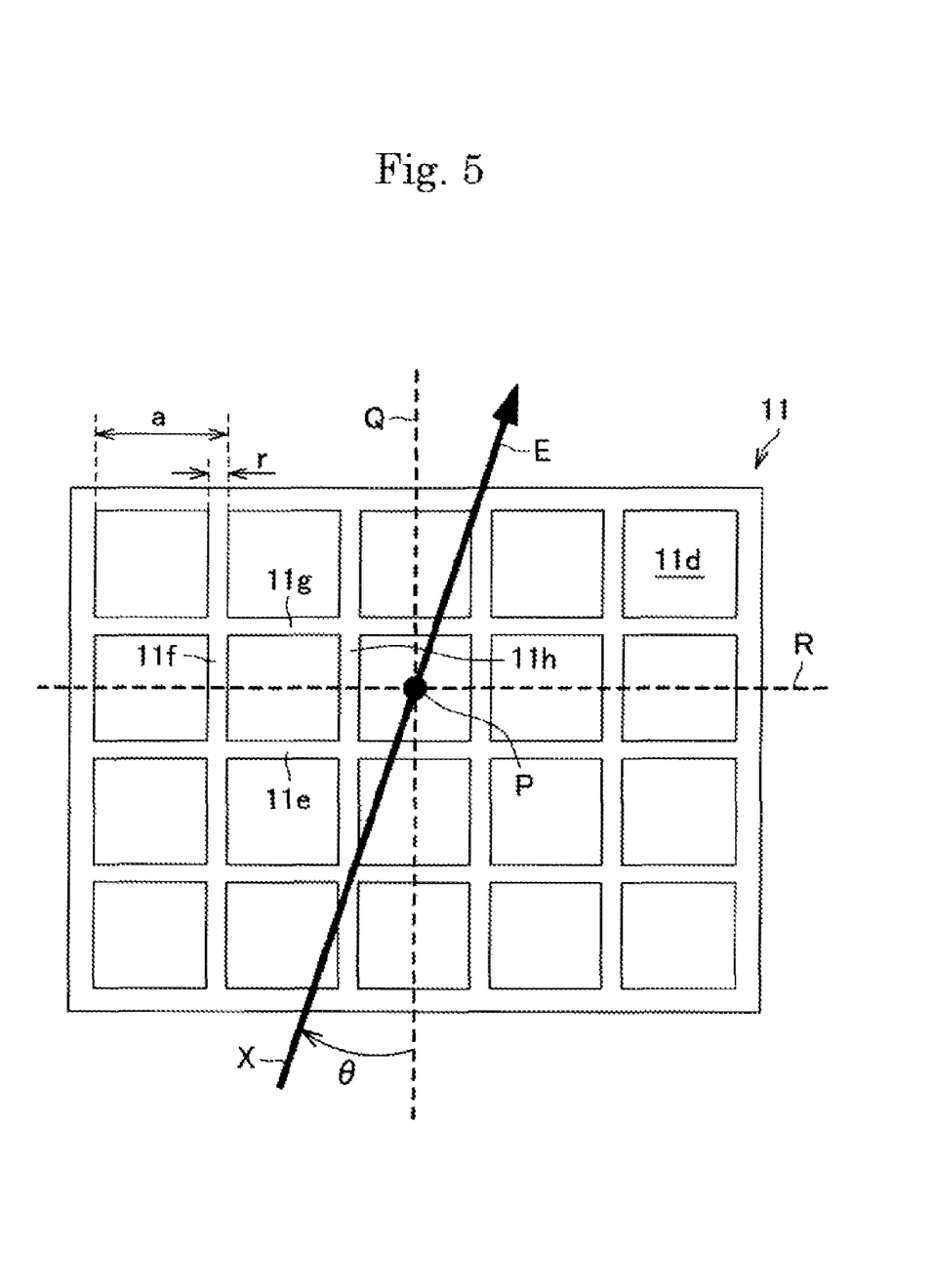
FIG. 5 is a diagram showing relationship of lattices and electromagnetic wave.

FIGS. 4 and 5 show positional relationship of the lattices of the ceramic honeycomb filter and electromagnetic wave.

Each trapping hole 11d of the filter 11 is partitioned with opposing first wall 11e and second wall 11g and opposing third wall 11f and fourth wall 11h. The trapping hole 11d is thereby shaped as a square lattice. Each trapping hole 11d is elongated between one end face 11b to the other end face 11c of the filter 11.

"P" is assigned to the longitudinal direction of each trapping hole 11d of the ceramic honeycomb filter 11. Here, in a plane (in the plane shown in FIGS. 4(b) and 5 perpendicular to the longitudinal direction P, electromagnetic wave X is transmitted and electromagnetic wave E after passing through the filter 11 is received, so that the particulates trapped in the filter is detected based on the intensity of the received electromagnetic wave. Here, the frequency of the electromagnetic wave is greater than or equal to 0.294 c/a or less than or equal to 1 c/a (a represents a lattice spacing of the trapping holes, and c represent the speed of light), the electromagnetic wave X is irradiated to the filter 11 which does not trap the particulates, and an inclined angle θ of the electromagnetic wave X with respect to an axis Q perpendicular to the first wall 11e and second wall 11g is changed so that the intensity of the received electromagnetic wave E becomes larger.

Here, although the lattice spacing a of the trapping holes is not limited, it may preferably be 0.5 mm or more and 5 mm or less on the viewpoint of performing the measurement of the distribution. When a is smaller than 0.5 mm, the frequency of the electromagnetic wave becomes larger than 600 GHz, so that the absorption by the ceramic filter becomes considerable and the measurement of the distribution becomes impossible. Further, when a is larger than 5 mm, the frequency of the electromagnetic wave becomes lower than 17 GHz to adversely affect the special resolution and the beam diameter of the electromagnetic wave is expanded to result in the interference of adjacent receptors of the electromagnetic waves, so that the measurement of the distribution becomes impossible.

The applicable range of the frequency depends on a and, for example, in the case that a is 5 mm, the frequency range is 17.64 GHz or higher and 60 GHz or lower. When it is used within the range, it is proved that the dependency of the transmittance on the angle of incidence is observed and that transmissible angle is changed within the frequency range so that the optimum range is present. In this case, even when a wall thickness r is changed while the lattice spacing is made constant, the dependency on the angle of incidence and the optimum range are not changed. In the case that the frequency is lower than 17.64 GHz, the dependency on the angle of incidence is proved to be smaller. In the case that the frequency is higher than 60 GHz, the deviation on the angle of incidence is proved to be large, so that the output of transmitted electromagnetic wave becomes unstable depending on changes of ambient conditions such as temperature. Similarly, in the case that a is 0.5 mm, the frequency range is proved to be 176.4 GHz or higher and 600 GHz or lower. Also in this case, the dependency on the angle of incidence and the optimum range described above are proved to be the same as those in the case that a is 5 mm.

Further, even when the porosity of the filter material is changed, it is confirmed that, although the effective refractive index of the ceramic part is changed, the characteristics shown in FIG. 6 is not changed.

As a transmitting device, the followings are preferred but are not limited.

(Frequency 30 Ghz to 100 Ghz)
MMIC such as GaAs or SiGe or GaN diode
(30 GHz to 10 THz)
An optical multiplying system adapted to generate the above-mentioned electromagnetic wave by generating high-order optical sideband waves by an LN modulator to take out a sideband wave of a desired order, and taking out a beat signal thereof by a photo mixer. In this case, a Mach-Zehnder optical modulator or phase modulator, or an integrated modulator thereof can be used as the LN modulator. Such LN modulator is not particularly limited. When a thin plate structure described in Japanese Patent Application Laid-Open No. 2007-79466A is used as the LN modulator, half-wavelength voltage can be reduced to generate the electromagnetic wave at a low driving voltage.

Further, a PPLN (Periodically Poled Lithium Niobate) device or PPLT (Periodically Poled Lithium Tantalate) device having a domain-inverted structure (QPM: Quasi-Phase Matching) formed thereon, and an optical waveguide (including a slab structure) device using angle phase matching or Cherenkov radiation can be used.

Examples of a receiving device include a shot key diode such as GaAs, InAs or GaN, a bolometer, and a device using pyroelectric effect.

The particulates mean substances having the property of being suspended within a gas, and the particle size thereof is typically 10 nm to 10 μm but is not limited. Examples of the substances constituting the particulates include, but are not particularly limited to, PM (particulate matter) mainly composed of carbon, hydrocarbon (HC), magnetic powder such as ferrite powder, sulfate, and nitrate.

According to a preferred embodiment, the frequencies of the electromagnetic waves transmitted from a plurality of the transmitting means are made different from each other. It is thereby possible to separately process information carried by the electromagnetic waves irradiated to the respective regions, so that it can be avoided an error of the measured value of the accumulation amount due to the interference of the electromagnetic waves.

According to this embodiment, on the viewpoint of preventing measurement error due to the interference of the electromagnetic waves, the difference of the frequencies of the electromagnetic waves may preferably be 30 GHz or more and more preferably be 80 GHz or more.

Further, according to a preferred embodiment, electromagnetic waves are transmitted from a plurality of the transmitting means by means of switching based on time sharing system. This means that the electromagnetic waves are not transmitted from a plurality of the transmitting means at the same time zone. It is thus possible to prevent the measurement error due to the interference of the electromagnetic waves.

The ceramic honeycomb filter is disposed within the container through which the gas containing particulates is distributed. The filter may preferably be made of a material having a specific dielectric constant of 1.5 or more and 10 or less. Further, the material may be cordierite, aluminum titanate, silicon nitride, alumina, silicon carbide, titanium oxide or the like. The mixture of the materials may be further used.

The frequency f of the electromagnetic wave may preferably be 70 to 200 GHz and more preferably be 80 to 170 GHz.

Although the inner diameter of the pipe is not limited, it may usually be 10 to 300 mm. Further, the inner diameter (maximum value) of the container may preferably be 20 mm or larger and preferably be 1000 mm or smaller.

The container preferably includes a storage part for storing the filter, an upstream connection part and a downstream connection part. In this case, the inside diameter of the storage part is larger than that of the pipe. It is preferred that the inside diameter of the upstream connection part is gradually reduced from the storage part toward the upstream pipe. It is also preferred that the inside diameter of the downstream connection part is gradually reduced from the storage part toward the downstream pipe.

In the present invention, the intensity of the electromagnetic wave received by the receiving means is detected, and the accumulation amount of particulates trapped in the filter is computed based on the intensity. Although a concrete method therefor is not limited, the accumulation amount of particulates is preferably computed by substituting the electromagnetic wave intensity detected by the electromagnetic wave receiving means in a predetermined relational expression between intensity and accumulation amount.

Since the filter itself absorbs the electromagnetic wave to some degree, the receiving intensity is preliminarily measured, as a blank, in a state in which no particulates are trapped. The accumulation amount of particulates is then calculated based on a difference between the blank and the received intensity in a state where the particulates are trapped and an electromagnetic wave absorption coefficient.

The electromagnetic wave absorption coefficient is expressed by a logarithm of electromagnetic wave transmissivity, and the transmissivity is a ratio of outgoing output to incoming output.

In the present invention, the exhaust emission control system may preferably further comprise a reducing agent supply means for supplying a reducing agent into the exhaust gas on the upstream side of the filter. The reducing agent may be directly supplied into the exhaust gas, or can be indirectly supplied to the exhaust gas by post-injecting the reducing agent into a cylinder. When the temperature of the filter is higher than the igniting temperature of the reducing agent, the reducing agent burns within the filter, and the filter is raised in temperature to, for example, 600° C. or higher by the combustion heat, whereby the filter can be regenerated. The reducing agent supply means includes a pump, an injector or the like. Further, an oxidization catalyst may be disposed on the upstream side of the filter, or a catalyst layer may be formed in the filter.

When the reducing agent supply means is used, a control means is desirably provided to control the drive of the reducing agent supply means based on a detection value of accumulation amount of particulates trapped in the filter. According to this, the reducing agent supply means can be driven at an optimum time to improve the fuel efficiency.

EXAMPLES

Example 1

According to the procedure described referring to FIGS. 1, 3, 4 and 5, it was measured the transmittance of the electromagnetic wave through a ceramic honeycomb filter which does not trap particulates.

Specifically, a DPE filter 11 was used. The filter had an outer diameter of $\phi$144 mm and a length of 152 mm. The filter was made of cordierite, had a specific dielectric constant of 1.7 and wall thickness of 340 μm. Each trapping hole has horizontal and vertical dimensions of 1130 μm with a lattice spacing a of 1470 μM. THz-TDS (Terahertz Time-domain Spectroscopy) system was used to measure the received intensity with the inclined angle $\theta$ variously changed.

Figure 7:
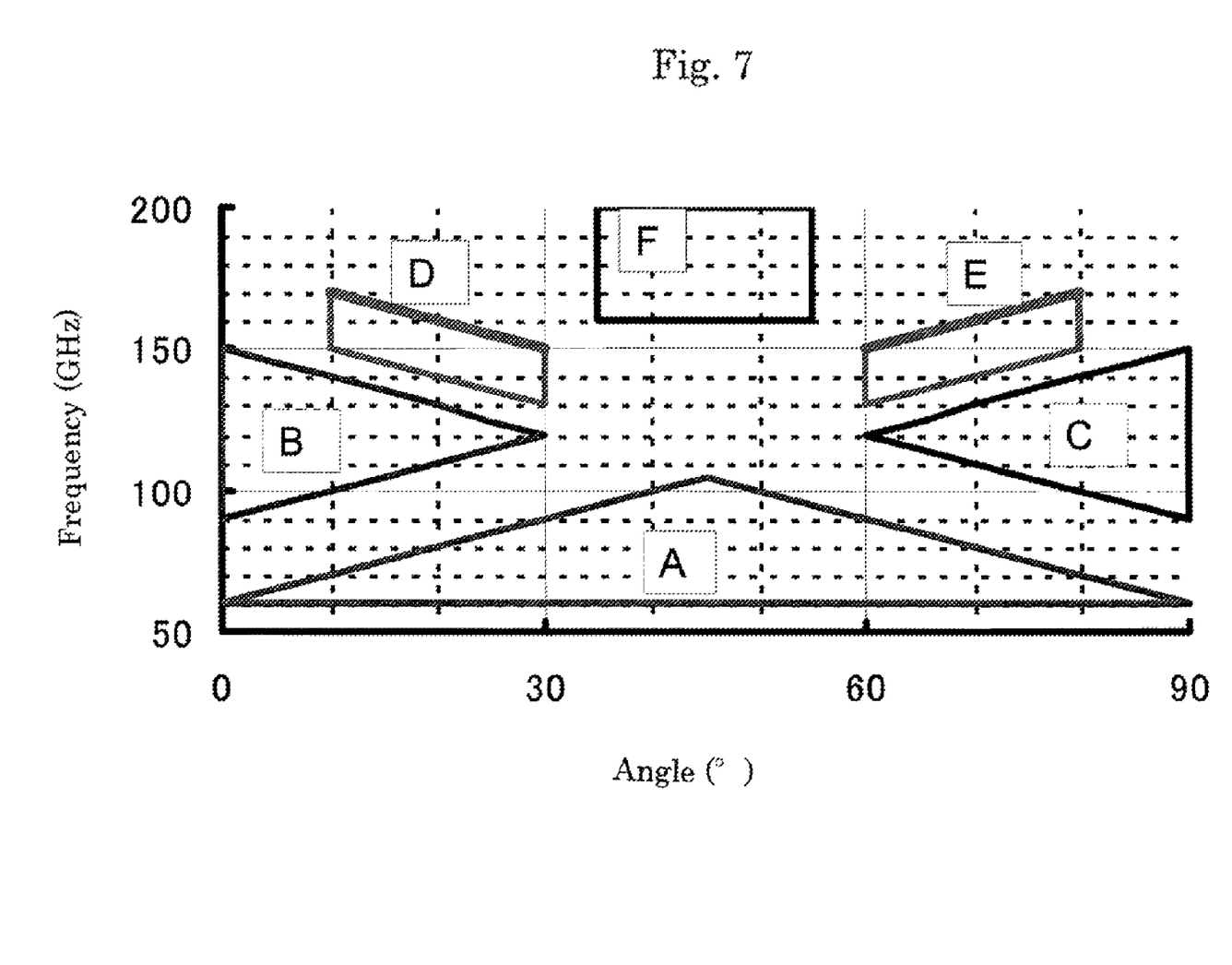
FIG. 7 is a graph showing relationship of an angle of incidence and frequency of electromagnetic wave in Example 1.

FIG. 7 shows relationship of the frequency of the electromagnetic wave and inclined angle. The received intensity of the electromagnetic wave transmitted through the filter could be measured only within regions A to F shown in FIG. 7. The loss was proved to be 10 dB or lower in the regions A, B and C, and 20 dB or lower in the regions D, E and F. It was not received in the other regions.

Figure 8:
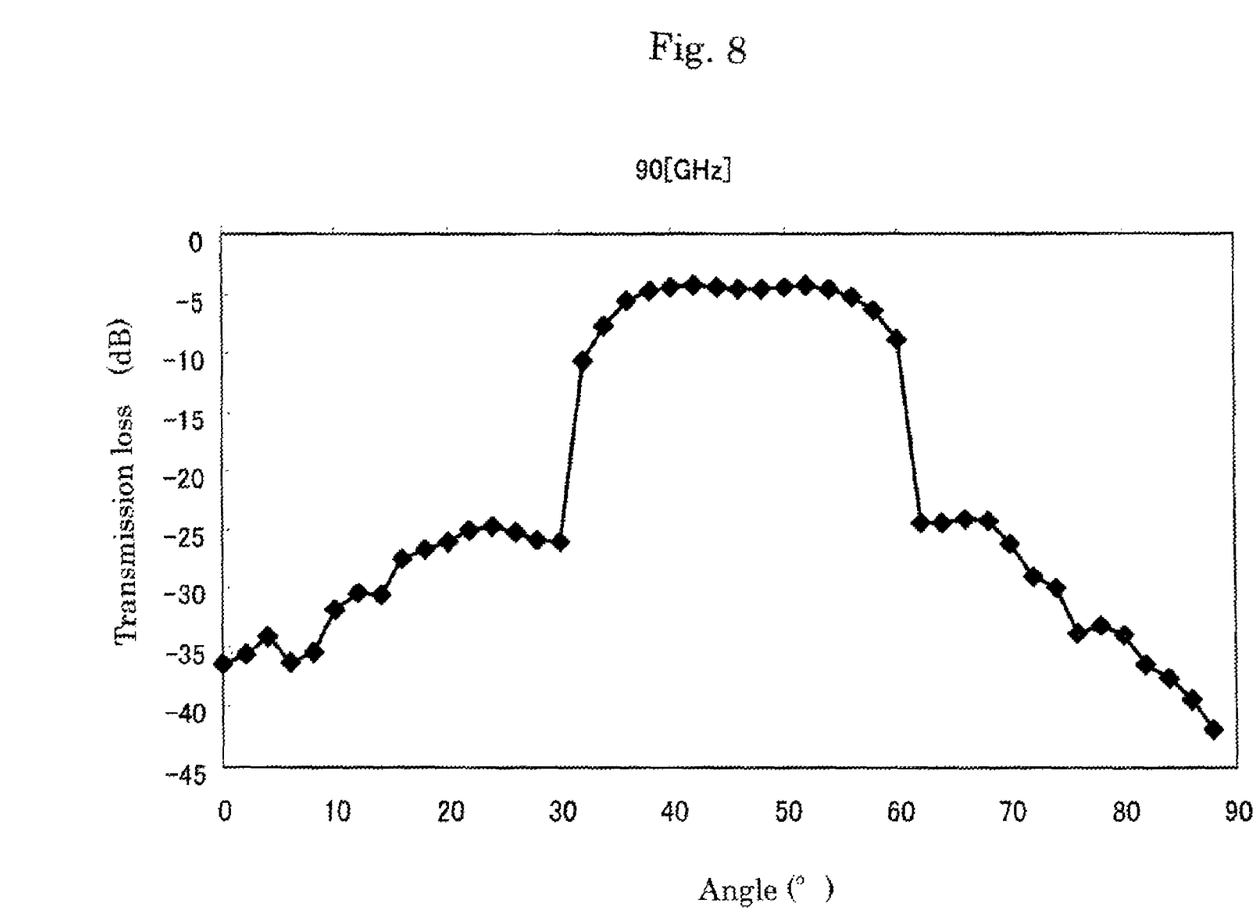
FIG. 8 is a graph showing relationship of the angle of incidence and transmission loss of electromagnetic wave with a frequency of 90 GHz in Example 1 (FIG. 7).
Figure 9:
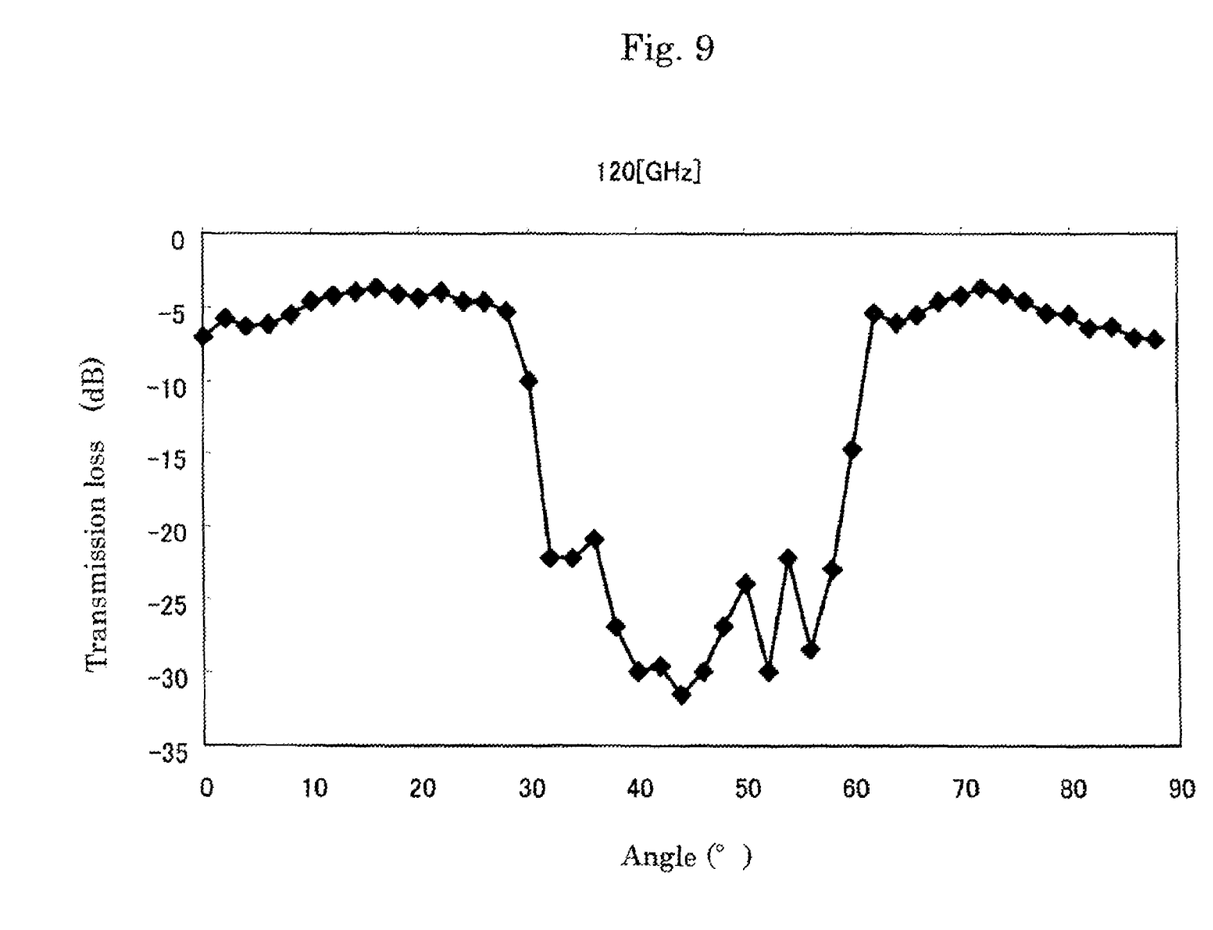
FIG. 9 is a graph showing relationship of the angle of incidence and transmission loss of electromagnetic wave with a frequency of 120 GHz in Example 1 (FIG. 7).

Here, FIGS. 8 and 9 are graphs showing characteristics of transmission at frequencies of 90 GHz and 120 GHz, respectively, obtained by frequency analysis of THz-TDS spectrum received in the present measurement.

FIG. 8 corresponds with the dependency on the angle $\theta$ of incidence at 90 GHz. At the frequency, it is measurable in the region A, and it was confirmed that the transmission loss was proved to be 10 dB or lower in the angle $\theta$ of 30° to 60° and that the incident electromagnetic wave could be propagated efficiently.

FIG. 9 corresponds with the dependency on the angle of incidence $\theta$ at 120 GHz in FIG. 7. It is measurable in the regions B and C at the frequency, and it was confirmed that the transmission loss was proved to be 10 dB or lower at the angle $\theta$ of 0° to 30° or 60° to 90°, and that the incident electromagnetic wave could be propagated efficiently.

Besides, although it is not shown here, at frequencies other than 90 and 120 GHz, it is obtained graphs similar to those shown in FIGS. 8 and 9 showing relationship of the transmission loss and angle of incidence, by frequency analysis of the THz-TDS spectrum of FIG. 7 obtained in the present measurement.

Example 2

Figure 10:
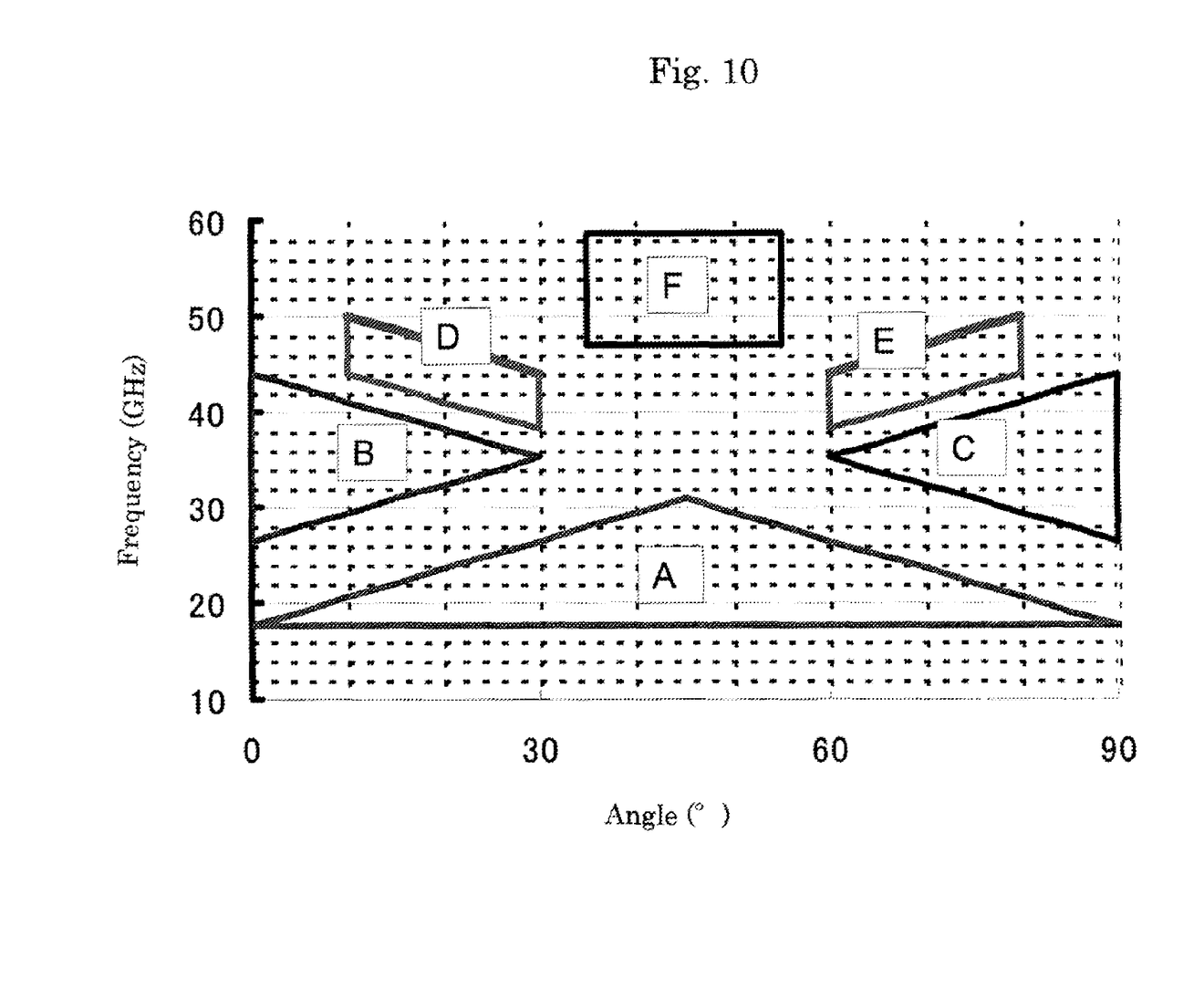
FIG. 10 is a graph showing relationship of the inclined angle and frequency of electromagnetic wave in Example 2.

According to the same procedure as the Example 1, the frequency f of the electromagnetic wave and the inclined angle $\theta$ were changed as shown in FIG. 10 to measure the received intensity of the electromagnetic wave passed through the filter. However, the wall thickness r was made 340 μm and lattice spacing a was made 5000 μm.

FIG. 10 shows relationship of the frequency of the electromagnetic wave and inclined angle. The received intensity of the electromagnetic wave transmitted through the filter was measurable only in regions A to F as shown in FIG. 10. The loss was proved to be 10 dB or lower in A, B and C and 20 dB or lower in D, E and F. It was not received in the other regions.

Besides, it is needless to say that the THz-TDS spectrum of FIG. 10 received by the present measurement was subjected to frequency analysis to obtain graphs showing relationship of the transmission loss and angle of incidence, similar to those shown in FIGS. 8 and 9.

Example 3

Figure 11:
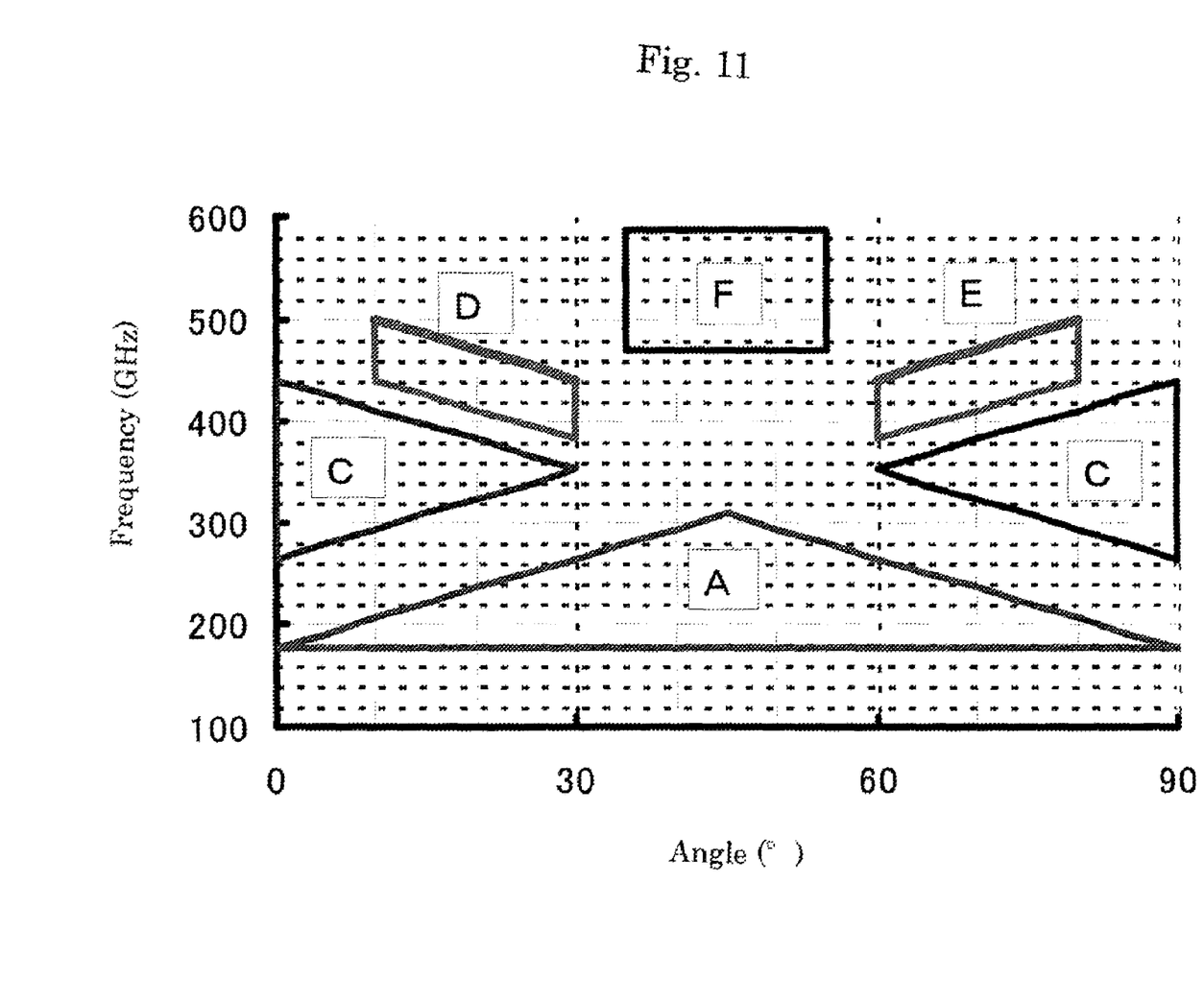
FIG. 11 is a graph showing relationship of the inclined angle and frequency of electromagnetic wave in Example 3.

According to the same procedure as the Example 1, the frequency f of the electromagnetic wave and the inclined angle θ were changed as shown in FIG. 11 to measure the received intensity of the electromagnetic wave through the filter. However, the wall thickness r was made 30 μm and lattice spacing a was made 500 μm.

FIG. 11 shows relationship of the frequency of the electromagnetic wave and inclined angle. The received intensity of the electromagnetic wave transmitted through the filter was measurable only in regions A to F as shown in FIG. 11. The loss was proved to be 10 dB or lower in A, B and C and 20 dB or lower in D, E and F. It was not received in the other regions.

Besides, it is needless to say that the THz-TDS spectrum of FIG. 11 received by the present measurement was subjected to frequency analysis to obtain graphs showing relationship of the transmission loss and angle of incidence, similar to those shown in FIGS. 8 and 9.

Although specific embodiments of the present invention have been described above, the present invention is not limited to the specific embodiments and can be carried out with various changes and modifications without departing from claims.

(Description Of Reference Numerals)
1 Diesel Engine
2 Discharge pipe
3 Upstream pipe
4 Downstream pipe
5 Container
8 Control unit
11 Ceramic honeycomb filter
11b, 11c End face
11d Trapping holes
11e First wall
11f Third wall
11g Second wall
11h Fourth wall
12 Particulates
a Lattice spacing of trapping holes
A, B Exhaust gas
E, X Electromagnetic wave
P Longitudinal direction of trapping hole 11d

The invention claimed is:

1. A method of detecting particulates, the method using a ceramic honeycomb filter comprising trapping holes for trapping said particulates from a gas containing said particulates to detect said particulates trapped in said ceramic honeycomb filter, said trapping holes forming lattices, said method comprising:
   transmitting an electromagnetic wave to said ceramic honeycomb filter in a plane perpendicular to the longitudinal direction of said trapping hole;
   receiving said electromagnetic wave after said electromagnetic wave passes through said ceramic honeycomb filter;
   detecting said particulates trapped in said filter based on a received intensity of said electromagnetic wave, wherein said electromagnetic wave has a frequency of greater than or equal to 0.294 c/a or less than or equal to 1 c/a (a represents a lattice spacing of said trapping holes and c represents the speed of light); and
   irradiating said electromagnetic wave to said ceramic honeycomb filter wherein said particulates are not trapped and changing an inclined angle of said electromagnetic wave with respect to said lattices so that a received intensity of said electromagnetic wave is increased.

2. The method of claim 1, wherein said lattice spacing a is 0.5 mm or larger and 5 mm or smaller.

3. The method of claim 1, wherein said ceramic honeycomb filter comprises a material having a specific dielectric constant of 1.5 or higher and 10 or lower.

4. The method of claim 1, wherein said material of said ceramic honeycomb filter comprises cordierite, aluminum titanate or silicon carbide.

5. A method of detecting particulates, the method using a ceramic honeycomb filter comprising trapping holes for trapping said particulates from a gas containing said particulates to detect said particulates trapped in said ceramic honeycomb filter, said trapping holes forming square lattices each partitioned by opposing first and second walls and opposing third and fourth walls, said method comprising:
   transmitting an electromagnetic wave to said ceramic honeycomb filter in a plane perpendicular to the longitudinal direction of said trapping hole;
   receiving said electromagnetic wave after said electromagnetic wave passes through said filter; and
   detecting said particulates trapped in said filter based on a received intensity of said electromagnetic wave,
   wherein the following relationships are satisfied:

$$a/\lambda \geq 0.294;$$

$$a/\lambda \leq 0.294 + 4.9 \times 10^{-3} \times \theta; \text{ and}$$

$$a/\lambda \leq 0.735 - 4.9 \times 10^{-3} \times \theta$$

(a represents a lattice spacing of said trapping holes, λ represents a wavelength of said electromagnetic wave, and θ represents an inclined angle of said electromagnetic wave with respect to an axis perpendicular to said first and second walls).

6. The method of claim 5, wherein said ceramic honeycomb filter comprises a material having a specific dielectric constant of 1.5 or higher and 10 or lower.

7. The method of claim 5, wherein said material of said ceramic honeycomb filter comprises cordierite, aluminum titanate or silicon carbide.

8. A method of detecting particulates, the method using a ceramic honeycomb filter comprising trapping holes for trapping said particulates from a gas containing said particulates to detect said particulates trapped in said ceramic honeycomb filter, said trapping holes forming square lattices each partitioned by opposing first and second walls and opposing third and fourth walls, said method comprising:
   transmitting an electromagnetic wave to said ceramic honeycomb filter in a plane perpendicular to the longitudinal direction of said trapping hole;
   receiving said electromagnetic wave after said electromagnetic wave passes through said filter; and
   detecting said particulates trapped in said filter based on a received intensity of said electromagnetic wave,
   wherein the following relationships are satisfied:

$$0.441 + 4.9 \times 10^{-3} \times \theta \leq a/\lambda \leq 0.735 - 4.9 \times 10^{-3} \times \theta; \text{ and}$$

$$0° \leq \Theta \leq 30°$$

(a represents a lattice spacing of said trapping holes, λ represents a wavelength of said electromagnetic wave, and θ represents an inclined angle of said electromagnetic wave with respect to an axis perpendicular to said first and second walls).

9. The method of claim 8, wherein said ceramic honeycomb filter comprises a material having a specific dielectric constant of 1.5 or higher and 10 or lower.

10. The method of claim 8, wherein said material of said ceramic honeycomb filter comprises cordierite, aluminum titanate or silicon carbide.

11. A method of detecting particulates, the method using a ceramic honeycomb filter comprising trapping holes for trapping said particulates from a gas containing said particulates to detect said particulates trapped in said ceramic honeycomb filter, said trapping holes forming square lattices each partitioned by opposing first and second walls and opposing third and fourth walls, said method comprising:
- transmitting an electromagnetic wave to said ceramic honeycomb filter in a plane perpendicular to the longitudinal direction of said trapping hole;
- receiving said electromagnetic wave after said electromagnetic wave passes through said ceramic honeycomb filter; and
- detecting said particulates trapped in said filter based on a received intensity of said electromagnetic wave,
- wherein the following relationships are satisfied:

$0.882-4.9\times10^{-3}\times\theta \leq a/\lambda \leq 0.294+4.9\times10^{-3}\times\theta$; and $60° \leq \Theta \leq 90°$ (a represents a lattice spacing of said trapping holes, $\lambda$ represents a wavelength of said electromagnetic wave, and $\theta$ represents an inclined angle of said electromagnetic wave with respect to an axis perpendicular to said first and second walls).

12. The method of claim 11, wherein said ceramic honeycomb filter comprises a material having a specific dielectric constant of 1.5 or higher and 10 or lower.

13. The method of claim 11, wherein said material of said ceramic honeycomb filter comprises cordierite, aluminum titanate or silicon carbide.

14. A method of detecting particulates, the method using a ceramic honeycomb filter comprising trapping holes for trapping said particulates from a gas containing said particulates to detect said particulates trapped in said ceramic honeycomb filter, said trapping holes forming square lattices each partitioned by opposing first and second walls and opposing third and fourth walls, said method comprising:
- transmitting an electromagnetic wave to said ceramic honeycomb filter in a plane perpendicular to the longitudinal direction of said trapping hole;
- receiving said electromagnetic wave after said electromagnetic wave passes through said ceramic honeycomb filter; and
- detecting said particulates trapped in said filter based on a received intensity of said electromagnetic wave,
- wherein the following relationships are satisfied:

$0.782-4.9\times10^{-3}\times\theta \leq a/\lambda \leq 0.882-4.9\times10^{-3}\times\theta$; and $10° \leq \theta \leq 30°$ (a represents a lattice spacing of said trapping holes, $\lambda$ represents a wavelength of said electromagnetic wave, and $\theta$ represents an inclined angle of said electromagnetic wave with respect to an axis perpendicular to said first and second walls).

15. The method of claim 14, wherein said ceramic honeycomb filter comprises a material having a specific dielectric constant of 1.5 or higher and 10 or lower.

16. The method of claim 14, wherein said material of said ceramic honeycomb filter comprises cordierite, aluminum titanate or silicon carbide.

17. A method of detecting particulates, the method using a ceramic honeycomb filter comprising trapping holes for trapping said particulates from a gas containing said particulates to detect said particulates trapped in said ceramic honeycomb filter, said trapping holes forming square lattices each partitioned by opposing first and second walls and opposing third and fourth walls, said method comprising:
- transmitting an electromagnetic wave to said ceramic honeycomb filter in a plane perpendicular to the longitudinal direction of said trapping hole;
- receiving said electromagnetic wave after said electromagnetic wave passes through said ceramic honeycomb filter; and
- detecting said particulates trapped in said filter based on a received intensity of said electromagnetic wave,
- wherein the following relationships are satisfied:

$0.343+4.9\times10^{-3}\times\theta \leq a/\lambda \leq 0.441+4.9\times10^{-3}\times\theta$; and $60° \leq \theta \leq 80°$ (a represents a lattice spacing of said trapping holes, $\lambda$ represents a wavelength of said electromagnetic wave, and $\theta$ represents an inclined angle of said electromagnetic wave with respect to an axis perpendicular to said first and second walls).

18. The method of claim 17, wherein said ceramic honeycomb filter comprises a material having a specific dielectric constant of 1.5 or higher and 10 or lower.

19. The method of claim 17, wherein said material of said ceramic honeycomb filter comprises cordierite, aluminum titanate or silicon carbide.

20. A method of detecting particulates, the method using a ceramic honeycomb filter comprising trapping holes for trapping said particulates from a gas containing said particulates to detect said particulates trapped in said ceramic honeycomb filter, said trapping holes forming square lattices each partitioned by opposing first and second walls and opposing third and fourth walls, said method comprising:
- transmitting an electromagnetic wave to said ceramic honeycomb filter in a plane perpendicular to the longitudinal direction of said trapping hole;
- receiving said electromagnetic wave after said electromagnetic wave passes through said ceramic honeycomb filter; and
- detecting said particulates trapped in said filter based on a received intensity of said electromagnetic wave,
- wherein the following relationships are satisfied:

$0.784 \leq a/\lambda \leq 0.98$; and $35° \leq \theta \leq 55°$ (a represents a lattice spacing of said trapping holes, $\lambda$ represents a wavelength of said electromagnetic wave, and $\theta$ represents an inclined angle of said electromagnetic wave with respect to an axis perpendicular to said first and second walls).

21. The method of claim 20, wherein said ceramic honeycomb filter comprises a material having a specific dielectric constant of 1.5 or higher and 10 or lower.

22. The method of claim 20, wherein said material of said ceramic honeycomb filter comprises cordierite, aluminum titanate or silicon carbide.

* * * * *